United States Patent
Arai et al.

(10) Patent No.: US 9,315,439 B2
(45) Date of Patent: Apr. 19, 2016

(54) METHOD FOR PRODUCING ALDEHYDE

(71) Applicant: Kao Corporation, Chuo-ku (JP)

(72) Inventors: Tsubasa Arai, Wakayama (JP); Jun Kono, Wakayama (JP); Takahiro Asada, Wakayama (JP); Ryo Nishimura, Wakayama (JP); Kunio Matsui, Tochigi (JP); Satoshi Kodama, Tochigi (JP)

(73) Assignee: Kao Corporation, Chuo-ku (JP)

( * ) Notice: Subject to any disclaimer, the term of this patent is extended or adjusted under 35 U.S.C. 154(b) by 0 days.

(21) Appl. No.: 14/411,315

(22) PCT Filed: Jun. 11, 2013

(86) PCT No.: PCT/JP2013/066087
§ 371 (c)(1),
(2) Date: Dec. 24, 2014

(87) PCT Pub. No.: WO2014/002751
PCT Pub. Date: Jan. 3, 2014

(65) Prior Publication Data
US 2015/0284310 A1  Oct. 8, 2015

(30) Foreign Application Priority Data

Jun. 27, 2012  (JP) ................. 2012-144546
Dec. 18, 2012  (JP) ................. 2012-275987

(51) Int. Cl.
C07C 45/00 (2006.01)
C07C 45/29 (2006.01)

(52) U.S. Cl.
CPC ............... *C07C 45/002* (2013.01); *C07C 45/29* (2013.01)

(58) Field of Classification Search
CPC .................................................. C07C 45/002
USPC ........................................................ 568/485
See application file for complete search history.

(56) References Cited

U.S. PATENT DOCUMENTS

| 4,383,124 | A | 5/1983 | De Graaf et al. |
| 7,235,701 | B2 * | 6/2007 | Hasegawa ............. B01J 29/072 568/471 |
| 7,795,475 | B2 | 9/2010 | Shirasawa et al. |
| 2004/0002620 | A1 | 1/2004 | Schwerin et al. |
| 2005/0272958 | A1 | 12/2005 | Hasegawa et al. |
| 2008/0292879 | A1 | 11/2008 | Kumamoto et al. |
| 2010/0010268 | A1 | 1/2010 | Shirasawa et al. |

FOREIGN PATENT DOCUMENTS

| JP | 2004-501881 | 1/2004 |
| JP | 2005-342675 | 12/2005 |
| JP | 2007-176897 | 7/2007 |
| JP | 2008-184452 | 8/2008 |
| WO | WO 2007/074922 A1 | 7/2007 |
| WO | WO 2008/093898 A1 | 8/2008 |

OTHER PUBLICATIONS

International Search Report issued Aug. 13, 2013, in PCT/JP13/066087 filed Jun. 11, 2013.
Extended European Search Report issued Oct. 22, 2015 in Patent Application No. 13808875.2.

* cited by examiner

*Primary Examiner* — Sikarl Witherspoon
(74) *Attorney, Agent, or Firm* — Oblon, McClelland, Maier & Neustadt, L.L.P.

(57) ABSTRACT

Provided is an aldehyde production method that can provide target aldehydes with excellent aldehyde selectivity and a high conversion for a long period of time. The method includes bringing a mixed gas containing a vaporized primary alcohol and an inert gas into contact with a film-type dehydrogenation catalyst so as to dehydrogenate the primary alcohol in the mixed gas, thereby obtaining an aldehyde. The partial pressure of the primary alcohol in the mixed gas is 50 kPa or lower, and the film-type dehydrogenation catalyst is formed by providing a thin film catalyst layer on a support.

20 Claims, 1 Drawing Sheet

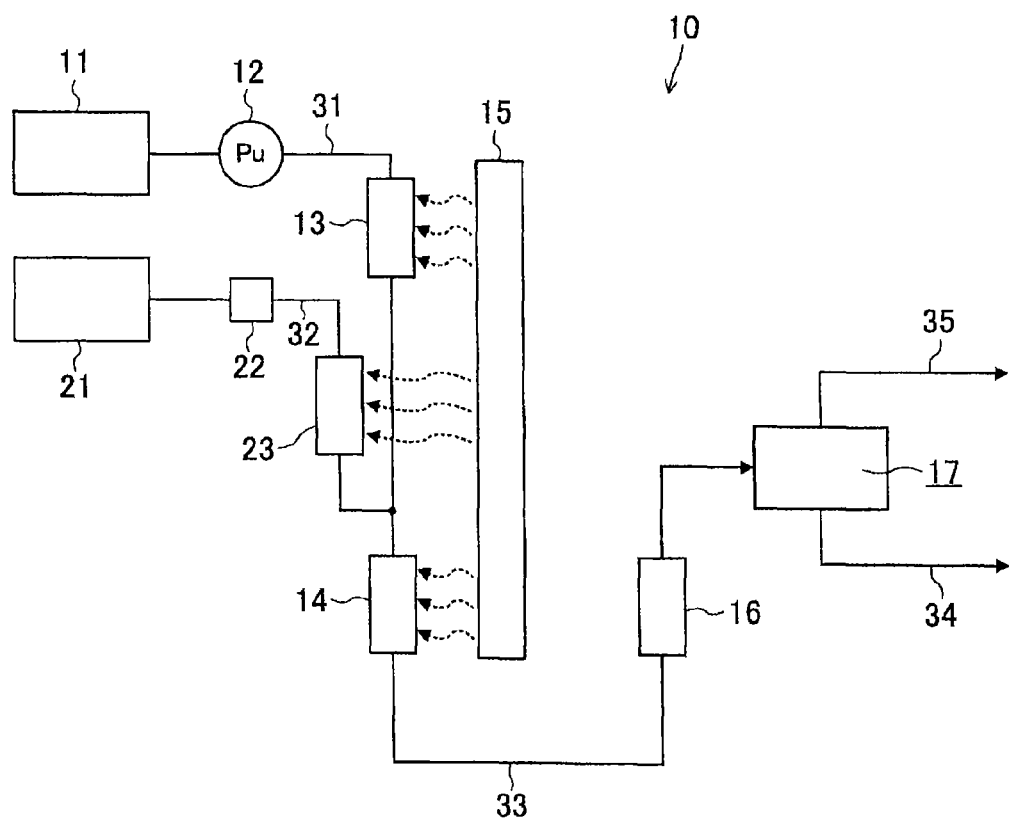

US 9,315,439 B2

METHOD FOR PRODUCING ALDEHYDE

CROSS REFERENCE TO RELATED APPLICATION

This application is a 371 of PCT/JP2013/066087, filed on Jun. 11, 2013, and claims priority to the following Japanese Applications: 2012-144546, filed on Jun. 27, 2012; and 2012-275987, filed on Dec. 18, 2012.

TECHNICAL FIELD

The present invention relates to a method for producing aldehydes.

BACKGROUND ART

Aldehydes are useful compounds as starting materials for chemical reaction and fragrance materials. Especially, aliphatic aldehydes having a specific molecular weight are useful as fragrance materials by themselves, and further used as starting materials for derivatives having different fragrance notes.

As methods for producing aldehydes, conventionally, dehydrogenation, oxidation reaction and the like that use alcohol as a starting material are known. Among these, since dehydrogenation is an endothermic reaction while oxidation reaction is an exothermic reaction, dehydrogenation is often adopted as the production method of aldehydes because thermal control of the reaction is easy. Accordingly, catalysts for dehydrogenation also have been studied.

For example, for the purpose of achieving high-yield production with easy process, Patent Document 1 discloses a production method of aldehydes by reacting alcohol in the presence of a film-type dehydrogenation catalyst for aldehyde production, which is used in aldehyde production using alcohol as a starting material.

For the purpose of improving yield and selectivity of aldehydes, Patent Document 2 discloses a production method of aldehydes in which fatty alcohol is continuously dehydrogenated in the presence of a copper/zinc oxide catalyst at a temperature of 200° C. to 280° C. and a pressure of 10 mbar to 1 bar.

PRIOR ART DOCUMENTS

Patent Documents

Patent Document 1: JP 2005-342675 A
Patent Document 2: JP 2004-501881 A

DISCLOSURE OF INVENTION

Problem to be Solved by the Invention

In the aldehyde production by alcohol dehydrogenation by a gas phase reaction, there are following problems. Since generated aldehydes vaporize from a catalyst slowly and reside on active sites on the catalyst for a long time, side reactions such as oligomerization between alcohol as a starting material and generated aldehydes occur, which reduces aldehyde selectivity. Further, as described above, since components that are less prone to volatilize, such as by-products and impurities contained in the starting material, are accumulated on the catalyst, deactivates the catalyst, which drops an alcohol conversion early. For these problems, the methods of Patent Documents 1 and 2 described above are not sufficient to continuously keep a high alcohol conversion and improve aldehyde selectivity.

An object of the present invention is to provide a method for producing aldehydes that can provide target aldehydes with excellent aldehyde selectivity and a high conversion for a long period of time.

Means for Solving Problem

The present inventors conducted studies based on the assumption that factors affecting a decrease in the conversion are conditions of a mixed gas as a starting material and a catalyst. As a result, it was found that in the aldehyde production in which primary alcohol is dehydrogenated, it is possible to obtain target aldehydes with a high conversion for a long period of time while improving the selectivity of obtained aldehydes by using a gas having a partial pressure of alcohol of 50 kPa or lower as a starting material and using a film-type dehydrogenation catalyst.

Specifically, the present invention provides a method for producing an aldehyde, the method including bringing a mixed gas containing a vaporized primary alcohol and an inert gas into contact with a film-type dehydrogenation catalyst so as to dehydrogenate the primary alcohol in the mixed gas, thereby obtaining an aldehyde. The partial pressure of the primary alcohol in the mixed gas is 50 kPa or lower, and the film-type dehydrogenation catalyst is formed by providing a thin film catalyst layer on a support.

Effect of the Invention

According to the present invention, it is possible to provide a method for producing aldehydes that can provide target aldehydes with excellent aldehyde selectivity and a high conversion for a long period of time.

BRIEF DESCRIPTION OF DRAWING

FIG. 1 is a block diagram showing a reaction device used in Example 1.

DESCRIPTION OF THE INVENTION

A method for producing an aldehyde of the present invention includes bringing a mixed gas containing a vaporized primary alcohol and an inert gas into contact with a film-type dehydrogenation catalyst so as to dehydrogenate the primary alcohol in the mixed gas, thereby obtaining an aldehyde. The partial pressure of the primary alcohol in the mixed gas is 50 kPa or lower, and the film-type dehydrogenation catalyst is formed by providing a thin film catalyst layer on a support.

The following are possible explanations about why the production method of the present invention can provide target aldehydes with excellent aldehyde selectivity and a high conversion for a long period of time.

In the present invention, by using the film-type dehydrogenation catalyst formed by providing a thin film catalyst layer on a support, a residence time of generated aldehydes in the catalyst becomes short as compared with the case of using other solid catalysts having deep pores. As a result, generated aldehydes can be suppressed from contacting with other molecules and the catalyst. Moreover, in the present invention, since primary alcohol is vaporized first and then brought into contact with the catalyst, the concentration of the primary alcohol per volume is lowered, which decreases side reactions involving plural molecules. Because of these reasons, according to the present invention, high aldehyde selectivity is obtained.

Moreover, in the present invention, by mixing the vaporized primary alcohol with an inert gas and bringing the mixed gas into contact with the dehydrogenation catalyst at a low alcohol partial pressure, the inert gas collides with compounds generated on the catalyst that will be precursors of high-molecular-weight components and impurities in the starting material, thereby promoting an elimination of the compounds that will be precursors of high-molecular-weight components and impurities in the starting material from the catalyst, and thus suppressing deactivation of the catalyst. Because of this, according to the present invention, it is possible to obtain target aldehydes with a high conversion for a long period of time.

In the present invention, the mixed gas used for dehydrogenation contains a vaporized primary alcohol and an inert gas.

The mixed gas containing a vaporized primary alcohol and an inert gas can be obtained by a method of mixing a vaporized primary alcohol and an inert gas, a method of mixing a primary alcohol before vaporization (i.e., in a liquid state) and an inert gas and thereafter vaporizing the primary alcohol, etc. In terms of uniformly mixing a primary alcohol and an inert gas, the mixed gas is preferably obtained by mixing a vaporized primary alcohol and an inert gas.

It is preferable that the primary alcohol is vaporized in advance by means of heating, decompression, etc. As conditions for vaporizing the primary alcohol, heating is preferred, and heating in a range of 200° C. to 500° C. is more preferred. The heating time is not particularly limited as long as it does not adversely affect the reaction. In terms of promoting vaporization while avoiding unnecessary heating to the alcohol, 10 seconds to 2 hours is preferred, and 5 minutes to 1 hour is further preferred.

In the case of heating, it is possible that the primary alcohol is placed in a container and the container is subjected to heating. The container for heating is not particularly limited as long as it does not adversely affect the reaction. Examples of the container include cylindrical tubes and spherical containers such as a stainless tube with a heat source and a flask equipped with oil bath. In terms of heating efficiency, a stainless tube is preferred.

The partial pressure of the primary alcohol in the mixed gas containing a vaporized primary alcohol and an inert gas is 50 kPa or lower, and preferably 30 kPa or lower in terms of suppressing deactivation of the catalyst. Also, in terms of obtaining aldehydes efficiently, the partial pressure of the primary alcohol is preferably 1 kPa or higher, and more preferably 5 kPa or higher. Moreover, in terms of promoting an elimination of by-products from the catalyst, suppressing deactivation of the catalyst, and obtaining aldehydes efficiently, the partial pressure of the vaporized primary alcohol in the mixed gas is preferably 1 to 50 kPa, and more preferably 5 to 30 kPa.

In the present invention, the mixed gas such as those described above is brought into contact with the film-type dehydrogenation catalyst so as to dehydrogenate the primary alcohol in the mixed gas. An exemplary method for bringing the mixed gas into contact with the film-type dehydrogenation catalyst is a method of passing the mixed gas through a reactor in which a film-type dehydrogenation catalyst is packed, thereby dehydrogenating alcohol in the reactor. Especially, a method of continuously passing the mixed gas through a reactor packed with a film-type dehydrogenation catalyst is preferred.

Examples of the reactor include a tubular flow reactor and a vessel-type reactor. In terms of quickly taking out generated aldehydes to the outside of the reactor, a tubular flow reactor is preferred.

When using the tubular flow reactor, it is preferable that, by a flow reactor that collects products continuously while supplying a mixed gas to a film-type dehydrogenation catalyst in the tube, the reaction is proceeded continuously or batch-wise by single flow or circulation supply. Also, a method for supplying the mixed gas may be either upflow or downflow. In terms of the alcohol conversion, downflow is preferred. Also, when using the vessel-type reactor, it is possible that a film-type dehydrogenation catalyst is installed inside, and the reaction is proceeded continuously or batch-wise, under stirring as needed.

The temperature of the dehydrogenation is preferably in a range of 200° C. to 300° C., and more preferably in a range of 230° C. to 270° C. in terms of the alcohol conversion. Also, the temperature of the dehydrogenation is preferably 200° C. or higher, and more preferably 230° C. or higher in terms of the alcohol conversion. Also, from the same view point, the temperature of the dehydrogenation is preferably 300° C. or lower, and more preferably 270° C. or lower.

In terms of vaporizing products, the pressure of the dehydrogenation is preferably 10 to 102 kPa. When the carbon number of the alcohol as a starting material is 10 or less, the pressure is preferably 80 to 102 kPa, and more preferably 101 kPa, i.e., an atmospheric pressure. When the carbon number of the alcohol as a starting material is 11 or more, the pressure is preferably 13 to 60 kPa.

The following describes respective components used in the present invention.

[Primary Alcohol]

In the present invention, an alcohol used as a starting material of aldehydes is a primary alcohol.

The carbon number of the alcohol is preferably 4 to 18, more preferably 4 to 15, and further preferably 6 to 12, in terms of usability of generated aldehydes as fragrance materials.

The alcohol may be either a saturated aliphatic alcohol or an unsaturated aliphatic alcohol. In terms of usability of generated aldehydes as fragrance materials, a saturated aliphatic alcohol is preferred. Especially, a saturated aliphatic alcohol with a carbon number of 4 to 18 is preferred, a saturated aliphatic alcohol with a carbon number of 4 to 15 is more preferred, and a saturated aliphatic alcohol with a carbon number of 6 to 12 is further preferred.

The alcohol has a straight chain, branched, or cyclic alkyl group or alkenyl group or alkynyl group. In terms of usability of generated aldehydes as fragrance materials, an alcohol having a straight chain or branched alkyl group is preferred, and an alcohol having a straight chain alkyl group is more preferred. Among these, an alcohol having a straight chain or branched alkyl group with a carbon number of 4 to 15 is preferred, and an alcohol having a straight chain alkyl group with a carbon number of 6 to 12 is preferred.

Specific examples of the alcohol include butanol, hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propylheptyl alcohol, lauryl alcohol, myristyl alcohol, geraniol, cyclopentyl methanol, cyclopentenyl methanol, cyclohexyl methanol, and cyclohexenyl methanol. Among these, in terms of usability of generated aldehydes as fragrance materials, hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, undecyl alcohol, 3,7-dimethyloctyl alcohol, 2-propylheptyl alcohol, lauryl alcohol, myristyl alcohol and geraniol are preferred, and hexyl alcohol, octyl alcohol, nonyl alcohol, decyl alcohol, undecyl alcohol and lauryl alcohol are more preferred, and octyl alcohol, undecyl alcohol and lauryl alcohol are more preferred.

[Inert Gas]

In the present invention, an inert gas is used to adjust the pressure of the mixed gas and the partial pressure of the alcohol, thereby removing by-products generated on active sites on the catalyst and impurities in the starting material. In terms of affinity and reactivity with a catalyst, the inert gas is preferably nitrogen or a rare gas (the group 18 elements), and nitrogen is preferred. Examples of the rare gas include argon, helium and the like, and argon is preferred.

[Film-Type Dehydrogenation Catalyst]

A film-type dehydrogenation catalyst used in the present invention is not limited as long as it is a dehydrogenation catalyst in the form of a film. For example, it is a dehydrogenation catalyst having a catalyst layer of 1 mm or less in thickness formed on a support. In this case, in terms of suppressing residence in pores of the catalyst layer and obtaining high aldehyde selectivity, the thickness of the dehydrogenation catalyst layer in the form of a film is preferably 400 μm or less, more preferably 100 μm or less, further preferably 50 μm or less, and still further preferably 30 μm or less. Also, in terms of securing the strength of the form of a film and obtaining durability in strength, the thickness of the dehydrogenation catalyst layer in the form of a film is preferably 0.01 μM or more, and more preferably 1 μm or more.

As the structure of the film-type dehydrogenation catalyst, any structure corresponding to the shape of a reactor can be selected. Examples of the film-type dehydrogenation catalyst include a dehydrogenation catalyst coating layer that is formed on a wall surface inside a tube, and a dehydrogenation catalyst that is molded in a thin plate shape to partition the interior of a tube into a plurality of axial flow paths. Both of them can be used suitably for a tubular flow reactor. Also, the film-type dehydrogenation catalyst may be a dehydrogenation catalyst coating layer that is formed on a surface of an open fin-shaped flat plate mounted inside a vessel, or the like. Such a film-type dehydrogenation catalyst can be used suitably for a vessel-type reactor. In terms of securing the surface of a catalyst body, on which a reaction starting material is supplied and a product is collected, as large as possible, and proceeding the reaction efficiently, the film-type dehydrogenation catalyst is preferably provided on bundled tubes each having an inner diameter of several millimeters to several dozen millimeters, or on an inner wall surface of a honeycomb structural body having a cell density of several dozen cells to several hundred cells per square inch.

In order to form the film-type dehydrogenation catalyst into the above structure, in terms of obtaining both a thin catalyst layer and a high mechanical strength, it is preferable to fix the catalytic active material on the surface of a support.

The support is preferably made of metal or other materials having stiffness, specific examples of which include a metallic foil, a carbon composite, and clay. Among these, a metallic foil is preferred. As the metallic foil, a copper foil, a stainless foil, an aluminum foil and the like are preferred, and a copper foil and a stainless foil are more preferred.

An example of the film-type dehydrogenation catalyst is a catalyst obtained by coating a support with a mixture of a catalytic active material and a binder, and curing the binder to fix the catalytic active material on the support.

An example of the binder used herein is a polymeric compound or an inorganic compound. Specific examples of the polymeric compound include cellulosic resin such as carboxymethylcellulose and hydroxyethylcellulose, fluorine resin such as polytetrafluoroethylene and polyvinylidene fluoride, urethane resin, epoxy resin, polyester resin, phenol resin, melamine resin, silicon resin and the like. Specific examples of the inorganic compound include inorganic compound sols such as silica and alumina.

Also, in the present invention, the film-type dehydrogenation catalyst is preferably a film-type dehydrogenation catalyst that is formed by providing a thin film catalyst layer containing a powdered catalyst and a silicon-containing resin as a binder on a support. In this case, the configuration is not limited as long as it is in the form of a thin film, and has a catalyst layer of 1 mm or less in thickness on the support, for example. In this case, in terms of suppressing residence in pores of the catalyst layer and obtaining high aldehyde selectivity, the thickness of the dehydrogenation catalyst layer in the form of a film is preferably 400 μm or less, more preferably 100 μm or less, further preferably 50 μm or less, and still further preferably 30 μm or less. Also, in terms of securing the strength of the form of a film and obtaining durability in strength, the thickness of the dehydrogenation catalyst layer in the form of a film is preferably 0.01 μm or more, and more preferably 1 μm or more.

In the present invention, in the case where the film-type dehydrogenation catalyst is a film-type dehydrogenation catalyst that is formed by providing a thin film catalyst layer containing a powdered catalyst and a silicon-containing resin as a binder on a support, the following is considered. Since the silicon-containing resin used as the binder of the film-type dehydrogenation catalyst has a higher affinity for a catalyst carrier having a smoother surface than for the catalytic active material that is fine crystal, the binder and the catalyst carrier adsorb to each other, thereby being fixed strongly. As a result, the powdered catalyst can be fixed on the support while preventing the binder from covering the surface of the catalytic active material, whereby a high initial conversion of the powdered catalyst can be obtained.

Also, in the case where the film-type dehydrogenation catalyst is a film-type dehydrogenation catalyst that is formed by providing on a support a thin film catalyst layer containing a powdered catalyst and a silicon-containing resin as a binder, the following is considered. Since the silicon-containing resin used as the binder also has excellent heat resistance and chemical resistance, it can keep the powdered catalyst fixed to the support for a long period of time as compared with other resins, even under a reaction condition that alcohol is supplied at high temperature. As a result, a state of the thin film in which a specific surface area of the powdered catalyst is large is kept for a long time. Moreover, as described above, since the catalyst carrier and the silicon resin adsorb to each other, the silicon-containing resin sufficiently covers the surface of the catalyst carrier, thereby preventing side reactions attributed to the catalyst carrier and accordingly suppressing generation of impurities such as high-molecular-weight components. Because of these reasons, according to the present invention in which the film-type dehydrogenation catalyst is the film-type dehydrogenation catalyst containing a powdered catalyst and a silicon-containing resin as a binder on a support, it is possible to obtain target aldehydes with a high conversion for a long period of time.

In the case of the film-type catalyst containing a silicon-containing resin as a binder, in terms of obtaining high aldehyde selectivity, the mass of the catalyst layer per unit area including the binder is preferably 0.015 g/m$^2$ or more, and more preferably 1.5 g/m$^2$ or more. Also, in the case of the film-type catalyst containing a silicon-containing resin as a binder, in terms of obtaining high aldehyde selectivity, the mass of the catalyst layer per unit area including the binder is preferably 600 g/m² or less, and more preferably 75 g/m² or less. Moreover, in the case of the film-type catalyst containing a silicon-containing resin as a binder, in terms of obtaining high aldehyde selectivity, the mass of the catalyst layer per unit area including the binder is preferably 0.015 g/m² to 600 g/m², and more preferably 1.5 g/m² to 75 g/m².

In the case of the film-type catalyst containing a silicon-containing resin as a binder, in terms of obtaining high aldehyde selectivity, the mass of a copper-based catalyst of the catalyst layer per unit area is preferably 0.01 g/m² or more, and more preferably 1.1 g/m² or more. Also, in the case of the film-type catalyst containing a silicon-containing resin as a binder, in terms of obtaining high aldehyde selectivity, the mass of the copper-based catalyst of the catalyst layer per unit area is preferably 440 g/m² or less, and more preferably 55 g/m² or less. Moreover, in the case of the film-type catalyst containing a silicon-containing resin as a binder, in terms of obtaining high aldehyde selectivity, the mass of the copper-based catalyst of the catalyst layer per unit area is preferably 0.01 g/m² to 440 g/m², and more preferably 1.1 g/m² to 55 g/m².

An example of the film-type dehydrogenation catalyst containing a silicon-containing resin as a binder is a catalyst obtained by coating the support with a mixture of the powdered catalyst and the silicon-containing resin, and curing the silicon-containing resin to fix the powdered catalyst on the support. A solvent may be added to the mixture to promote mixing and uniformity.

The solvent is not limited as long as it does not adversely affect catalytic activity of the powdered catalyst. The solvent preferably has favorable binder solubility, and may be used in combination of two or more kinds.

Examples of the solvent include water, alcohols, ketones, ethers, esters, hydrocarbons, halides and the like. Among these, water, alcohols, ketones and ethers are preferred, and alcohols and ketones are more preferred. Examples of the alcohols include methanol, ethanol, n-propanol, isopropanol, n-butanol, sec-butanol, t-butanol and the like. Among these, methanol, ethanol, and isopropanol are preferred. Examples of the ketones include acetone, methyl ethyl ketone, methyl isopropyl ketone, methyl isobutyl ketone, diethyl ketone and the like. Among these, acetone, methyl ethyl ketone, and methyl isobutyl ketone are preferred.

In the case of the film-type dehydrogenation catalyst containing a silicon-containing resin as a binder, the binder to be used is a silicon-containing resin, in terms of obtaining a high alcohol conversion. Examples of the silicon-containing resin include polycarbosilane, polysiloxane, polyborosiloxane, polytitanosiloxane, polysilazane, polyorganoaminosilane, polysilastyrene, polytitanocarbosilane, polyzirconocarbosilane, and polyorganosiloxane. In terms of the alcohol conversion, polytitanocarbosilane and polyorganosiloxane are preferred, and polytitanocarbosilane are more preferred.

Polytitanocarbosilane is a resin having a silicon-oxygen bond, a silicon-carbon bond, and a titanium-oxygen bond. Polytitanocarbosilane is a resin obtained by reacting polycarbosilane with titanium alkoxide, and the main chain part is composed of a silicon-oxygen-titanium bond and a silicon-carbon bond. Specifically, polytitanocarbosilane has a configuration in which a unit structure of a polymer chain of polycarbosilane is partially substituted with titanium alkoxide, or titanium alkoxide is bonded to a polymer chain of polycarbosilane as a pendant side chain, or titanium alkoxide forms cross-links between two or more polycarbosilanes. The polycarbosilane has a main chain skeleton represented by general formula —(SiRR'—CH$_2$)— (in the formula, R and R' are substituents), and the titanium alkoxide is represented by general formula Ti (OR")$_4$ (in the formula, R" is a substituent).

Examples of the substituents (the above R and R') bonded to a silicon atom by the silicon-carbon bond include an alkyl group, an aryl group, a vinyl group and the like. Among these, an alkyl group and an aryl group are preferred, an alkyl group is more preferred, and a combination of an alkyl group and an aryl group is further preferred.

The alkyl group is preferably an alkyl group with a carbon number of 1 to 18, more preferably an alkyl group with a carbon number of 1 to 6, and further preferably an alkyl group with a carbon number of 1 to 3. Specific examples of the alkyl group include a methyl group, an ethyl group and the like, and a methyl group is preferred.

The aryl group is preferably an aryl group with a carbon number of 6 to 20, more preferably an aryl group with a carbon number of 6 to 16, and further preferably an aryl group with a carbon number of 6 to 10. Specific examples of the aryl group include a phenyl group, a naphthyl group and the like, and a phenyl group is preferred.

The alkyl group, the aryl group, and the vinyl group may be substituted further with a substituent, examples of which include a hydroxyl group, an alkoxy group, a cyano group, a halogen atom and the like.

Polyorganosiloxane is a resin having a silicon-oxygen bond and a silicon-carbon bond, and the main chain part is composed of a silicon-oxygen bond. The side chain part is a substituent bonded to a silicon atom, and the substituent is bonded to the main chain part via the silicon-oxygen bond or silicon-carbon bond.

Examples of the substituent bonded to a silicon atom by the silicon-carbon bond include an alkyl group, an aryl group, a vinyl group and the like. Among these, an alkyl group and an aryl group are preferred, and an alkyl group is more preferred, and a combination of an alkyl group and an aryl group is further preferred.

The alkyl group is preferably an alkyl group with a carbon number of 1 to 18, more preferably an alkyl group with a carbon number of 1 to 6, and further preferably an alkyl group with a carbon number of 1 to 3. Specific examples of the alkyl group include a methyl group, an ethyl group and the like, and a methyl group is preferred.

The aryl group is preferably an aryl group with a carbon number of 6 to 20, more preferably an aryl group with a carbon number of 6 to 16, and further preferably an aryl group with a carbon number of 6 to 10. Specific examples of the aryl group include a phenyl group, a naphthyl group and the like, and a phenyl group is preferred.

The alkyl group, the aryl group, the vinyl group, and the like may be substituted further with a substituent, examples of which include a hydroxyl group, an alkoxy group, a cyano group, a halogen atom and the like.

Examples of the substituent bonded to a silicon atom by the silicon-oxygen bond include a hydroxyl group, an alkoxy group and the like.

The silicon-containing resin used in the film-type dehydrogenation catalyst containing a silicon-containing resin as a binder may be a resin having a straight chain structure, a branched structure, a cyclic structure, or the like. In terms of fixing the powdered catalyst, the resin as a binder preferably has a cross-linked structure.

It is preferable that the cross-linked structure is formed after coating a support with a mixture of a catalytic active material as a powdered catalyst and a binder, using a silicon-containing resin having a reactive substituent in a part thereof.

Examples of the method for forming a cross-linked structure include heating and light irradiation. In view of removing volatile components, heating is preferred.

The heating for forming a cross-linked structure is preferably performed by a method of spraying a heating medium that is obtained by heating air, water vapor, an inert gas such as nitrogen and argon, or the like. Other examples thereof include a method of utilizing radiant heat such as infrared radiation and far infrared radiation, and a heating system using induced current by electromagnetic waves. These methods can be used in combination. As the heating medium, air or nitrogen is preferred.

The heating conditions for forming a cross-linked structure are preferably such that a heating medium is sprayed at a temperature in a range of 60° C. to 400° C., preferably in a range of 100° C. to 360° C., and more preferably in a range of 150° C. to 320° C. for 10 minutes to 5 hours, preferably for 30 minutes to 4 hours, and more preferably for 45 minutes to 3 hours.

The weight ratio of the powdered catalyst and the silicon-containing resin is preferably the powdered catalyst:the silicon-containing resin=85:15 to 15:85, more preferably the powdered catalyst:the silicon-containing resin=83:17 to 50:50, and further preferably the powdered catalyst:the silicon-containing resin=80:20 to 60:40.

An exemplary method for obtaining the film-type dehydrogenation catalyst is a method of forming a coating layer containing the catalytic active material on the surface of a tubular, planar, honeycomb support or the like. As the coating method at this time, any conventionally known method can be used. Examples of the coating method include physical vapor deposition such as sputtering, chemical vapor deposition, and an impregnation method from a solution system as well as a method of applying a mixture of a catalytic active material and a binder using a bar coater, a blade, spraying, dipping, spinning, gravure, die-coating, or the like.

(Powdered Catalyst)

It is preferable that the catalytic active material of the present invention is used in the form of a powdered catalyst. The powdered catalyst may be a catalyst in which only a catalytic active material is powdered, but is preferably supported on a carrier. The carrier is preferably selected from the group consisting of oxides and hydroxides of aluminum, zinc, silicon, titanium and the like, zeolite, and silica-alumina. In terms of the alcohol conversion, the carrier is more preferably an oxide or a hydroxide of zinc or aluminum, and further preferably an oxide of zinc or an oxide or a hydroxide of aluminum.

In terms of the alcohol conversion, it is preferable that a suitably used powdered catalyst contains copper as an active species, i.e., a copper-based powdered catalyst. The copper-based powdered catalyst is preferably composed of copper alone, or composed of two components or three or more components containing copper and other metallic elements. Preferable examples of the other metallic elements contained in the copper-based powdered catalyst include iron, zinc, chromium, cobalt, nickel, manganese and the like. In terms of aldehyde selectivity, environmental friendliness and safety, iron and zinc are more preferred, and iron is further preferred. As the copper-based powdered catalyst, CuFeAl, CuZn, and the like are preferred.

The powdered catalyst as a composition containing a carrier is preferably a catalyst containing copper-iron-aluminum (CuFeAl). The atomic ratio of the elements constituting the catalyst is preferably (copper/iron/aluminum)=1/0.4-2.5/0.5-5.0, and more preferably 1/0.5-1.0/1.5-3.5. Also, the powdered catalyst as a composition containing a carrier is preferably a catalyst containing copper-zinc (CuZn). The atomic ratio of the elements constituting the catalyst is preferably (copper/zinc)=1/0.5-2.0, and more preferably 1/0.7-1.4.

(Production of Powdered Catalyst)

The production method of the powdered catalyst is not limited as long as the catalyst can promote dehydrogenation. The catalyst containing copper-iron-aluminum, which is a suitable mode of the catalyst, is preferably produced by a method in which the following first to third steps are performed in this order.

(First Step)

The first step is a step of suspending at least one kind selected from the group consisting of oxides and hydroxides of aluminum, silicon, titanium, zirconium, magnesium and iron, zeolite, and silica-alumina (hereinafter, referred to as a carrier) in an aqueous medium, and reacting a water-soluble copper salt and a water-soluble iron salt with an alkali substance in the suspension, thereby precipitating a copper compound and an iron compound on the surface of the carrier.

First, a water-soluble copper salt and a water-soluble iron salt are dissolved in water so that the atomic ratio of Cu/Fe is 1/0.4-2.5. In this aqueous solution, a carrier is suspended so that the atomic ratio of Cu/metallic atom of the carrier is 1/0.1-3.0. The suspension is heated to a temperature of 60° C. to 120° C., and an aqueous solution of an alkali substance in an amount corresponding to the total of equivalent numbers of copper and iron ions is added to the heated suspension, whereby a copper compound and an iron compound are precipitated on the surface of the catalyst carrier.

Examples of the water-soluble copper salt used in the present invention include cupric sulfate, cupric chloride, cupric nitrate and the like. A mixture of these also can be used. Examples of the water-soluble iron salt used in the present invention include ferrous sulfate, ferrous chloride, ferrous nitrate and the like. A mixture of these also can be used, but ferrous sulfate is suitable from an economical viewpoint.

An example of the alkali substance used in the present invention is a hydroxide, a carbonate or the like of alkali metal or alkaline-earth metal. Although the method of adding the alkali substance to the suspension is not limited particularly, these alkali substances are generally added in the form of an aqueous solution considering operability. When a hydroxide of alkali metal or alkaline-earth metal is used as the alkali substance, it is desirable to drop it slowly so as not to impair filterability of the precipitated catalyst. In the present invention, it is suitable to use a carbonate of alkali metal. The concentration of these alkali substances can be selected arbitrarily. Considering productivity of the catalyst, a highly concentrated precipitant also can be used. For example, in the case of sodium carbonate, an aqueous solution containing sodium carbonate in a concentration of 20 to 23% by mass is appropriate.

As to the carrier used in the first step, i.e., at least one kind selected from the group consisting of oxides and hydroxides of aluminum, silicon, titanium, zirconium, magnesium and iron, zeolite, and silica-alumina, it may be used directly after being prepared in a reaction vessel, or it may be a carrier prepared separately in advance. It is preferable that these carriers have a relatively uniform particle diameter. An average particle diameter of the carrier is 0.1 μm to 500 μm, and preferably 0.4 μm to 50 μm. An exemplary method for preparing the carrier in the reaction vessel is a method of dissolving into water a ferric salt such as a sulfate, a nitrate, and a hydrochloride in an amount to be used as the carrier, and dropping therein a carbonate of alkali metal, e.g., a sodium carbonate aqueous solution, at a temperature of 60° C. or higher in an amount corresponding to an equivalent number of iron ions so as to neutralize the solution. In this method, by charging a copper salt and an iron salt into the slurry without purifying a generated precipitate, the first step can be performed continuously. If carriers having uniform properties are used, it is possible to produce a catalyst with further stable performance. Therefore, the use of carriers having uniform properties is further advantageous in industrial-scale production.

(Second Step)

The second step is a step of reacting water-soluble aluminum with an alkali substance in the suspension obtained in the first step, thereby precipitating an aluminum compound on the surface of solid particles present in the suspension obtained in the first step.

The second step is performed by dropping, in the suspension obtained in the first step, (i) an aqueous solution of a water-soluble aluminum salt (where the Al amount in this case with respect to the water-soluble copper salt used in the first step is Cu/Al=1/0.1-5.0 and preferably 1/0.5-3.0 in the atomic ratio) and (ii) an alkali substance in an amount corresponding to an equivalent number of aluminum ions described in (i) above; and precipitating an aluminum compound while keeping the temperature of the suspension at 60° C. to 120° C.

Examples of the water-soluble aluminum salt described in (i) above include aluminum sulfate, aluminum chloride, aluminum nitrate, and various alums. Among these, aluminum sulfate is suitable. Further, a mixture of these also can be used.

Examples of the alkali substance described in (ii) above include the alkali substances to be used in the first step. The method of adding the alkali substance is preferably addition in the form of an aqueous solution in terms of operability. The concentration of the alkali substance is not limited particularly, and an aqueous solution containing the alkali substance in a concentration of about 20% by mass is preferred from an economical viewpoint. In order to prevent a rapid change of pH of the suspension, the method of adding the alkali substance is preferably such that the aqueous solution described in (i) above and the alkali substance or the solution thereof described in (ii) above are added simultaneously to the suspension.

Exemplary embodiments of the second step are as follows: (a) precipitating only an aluminum compound; (b) precipitating an aluminum compound and a copper compound simultaneously; (c) precipitating an aluminum compound and a copper compound simultaneously in the first stage, and precipitating an aluminum compound in the second stage; d) repeating a combination of these steps several times. A suspension obtained in the above-described method is adjusted at a pH of 7.0 or higher, and aged for 0 to 8 hours.

(Third Step)

In the third step, the precipitate obtained in the second step is separated by an ordinary method and washed with water. The obtained slurry or powder is dried and calcined. The calcining temperature is normally in a range of 100° C. or higher and 1200° C. or lower, and preferably in a range of 400° C. or higher and 900° C. or lower. The calcining time is not limited particularly, and 10 hours or less is preferred from an economical viewpoint. The resultant after calcining may be pulverized, and it can be also used directly as a catalyst without pulverization.

Regarding the above-described embodiment, the present invention further discloses the following aldehyde production method.

<1> A method for producing an aldehyde, including bringing a mixed gas containing a vaporized primary alcohol and an inert gas into contact with a film-type dehydrogenation catalyst so as to dehydrogenate the primary alcohol in the mixed gas, thereby obtaining an aldehyde, wherein the partial pressure of the primary alcohol in the mixed gas is 50 kPa or lower, and the film-type dehydrogenation catalyst is formed by providing a thin film catalyst layer on a support.

<2> The method for producing an aldehyde according to <1> above, wherein the dehydrogenation catalyst contains copper as an active species, and preferably is composed of copper alone or composed of two components or three or more components containing copper and other metallic elements, and more preferably is CuFeAl or CuZn.

<3> The method for producing an aldehyde according to <2> above, wherein the dehydrogenation catalyst further contains iron, zinc, chromium, cobalt, nickel, manganese, or the like, as an active species, preferably contains zinc or iron, and more preferably contains iron.

<4> The method for producing an aldehyde according to any one of <1> to <3> above, wherein the inert gas contains nitrogen or a rare gas (e.g., argon, helium, etc., preferably argon), and preferably contains nitrogen.

<5> The method for producing an aldehyde according to any one of <1> to <4> above, wherein the reaction temperature is 200° C. or higher, preferably 230° C. or higher, and 300° C. or lower, preferably 270° C. or lower, preferably in a range of 200° C. to 300° C., and preferably in a range of 230° C. to 270° C.

<6> The method for producing an aldehyde according to any one of <1> to <5> above, wherein the reaction pressure is in a range of 10 kPa to 102 kPa.

<7> The method for producing an aldehyde according to any one of <2> to <6> above, wherein the dehydrogenation catalyst is supported by a carrier.

<8> The method for producing an aldehyde according to <7> above, wherein the carrier is selected from the group consisting of oxides and hydroxides of aluminum, zinc, silicon and titanium, zeolite, and silica-alumina, preferably an oxide or a hydroxide of zinc or aluminum, and more preferably an oxide of zinc or an oxide or a hydroxide of aluminum.

<9> The method for producing an aldehyde according to <7> or <8> above, wherein the dehydrogenation catalyst as a composition containing a carrier is CuFeAl (the atomic ratio of copper/iron/aluminum is preferably (copper/iron/aluminum)=1/0.4-2.5/0.5-5.0, and more preferably 1/0.5-1.0/1.5-3.5), or CuZn (the atomic ratio of copper/zinc is preferably (copper/zinc)=1/0.5-2.0, and more preferably 1/0.7-1.4).

<10> The method for producing an aldehyde according to any one of <1> to <9> above, wherein the partial pressure of the primary alcohol is 50 kPa or lower, preferably 30 kPa or lower, and more preferably 15 kPa or lower.

<11> The method for producing an aldehyde according to any one of <1> to <10> above, wherein the partial pressure of the primary alcohol is 1 kPa or higher, and preferably 5 kPa or higher.

<12> The method for producing an aldehyde according to any one of <1> to <11> above, wherein the carbon number of the primary alcohol is 4 to 18, preferably 4 to 15, and more preferably 6 to 12.

<13> The method for producing an aldehyde according to any one of <1> to <12> above, wherein the primary alcohol is a saturated aliphatic alcohol with a carbon number of 4 to 18, preferably a saturated aliphatic alcohol with a carbon number of 4 to 15, and more preferably a saturated aliphatic alcohol with a carbon number of 6 to 12.

<14> The method for producing an aldehyde according to any one of <1> to <13> above, wherein the primary alcohol has a straight chain, branched, or cyclic alkyl group or alkenyl group or alkynyl group, preferably has a straight chain or branched alkyl group, more preferably has a straight chain alkyl group, further preferably has a straight chain or branched alkyl group with a carbon number of 4 to 15, and still further preferably has a straight chain alkyl group with a carbon number of 6 to 12.

<15> The method for producing an aldehyde according to any one of <1> to <12> above, wherein the carbon number of the primary alcohol is 10 or less, and the reaction pressure is 80 to 102 kPa, and preferably 101 kPa.

<16> The method for producing an aldehyde according to any one of <1> to <12> above, wherein the carbon number of the primary alcohol is 11 or more, and the reaction pressure is 13 to 60 kPa.

<17> The method for producing an aldehyde according to any one of <1> to <16> above, wherein the support is made of metal or other materials having stiffness, examples of which include a metallic foil, a carbon composite and clay, and a metallic foil is preferred (preferably, a copper foil, a stainless foil, an aluminum foil, and the like, and more preferably a copper foil and a stainless foil).

<18> The method for producing an aldehyde according to any one of <1> to <17> above, wherein the dehydrogenation catalyst is a film-type dehydrogenation catalyst that is formed by providing on a support a thin film catalyst layer containing a powdered catalyst and a silicon-containing resin as a binder.

<19> The method for producing an aldehyde according to any one of <1> to <18> above, wherein the silicon-containing resin is polycarbosilane, polysiloxane, polyborosiloxane, polytitanosiloxane, polysilazane, polyorganoaminosilane, polysilastyrene, polytitanocarbosilane, polyzirconocarbosilane, or polyorganosiloxane, and preferably polyorganosiloxane or polytitanocarbosilane, and more preferably polytitanocarbosilane.

<20> The method for producing an aldehyde according to any one of <1> to <19> above, wherein the weight ratio of the powdered catalyst and the silicon-containing resin (the powdered catalyst:the silicon-containing resin) is 85:15 to 15:85, preferably 83:17 to 50:50, and more preferably 80:20 to 60:40.

<21> The method for producing an aldehyde according to any one of <1> to <20> above, wherein the thickness of the catalyst layer is 1 mm or less, preferably 400 µm or less, more preferably 100 µm or less, further preferably 50 µm or less, still further preferably 30 µm or less, preferably 0.01 µm or more, and more preferably 1 µm or more.

<22> The method for producing an aldehyde according to any one of <1> to <21> above, wherein the film-type dehydrogenation catalyst is a catalyst obtained by coating the support with a mixture of the powdered catalyst and the silicon-containing resin and curing the silicon-containing resin to fix the powdered catalyst on the support.

<23> The method for producing an aldehyde according to any one of <1> to <22> above, wherein the step of bringing the gas into contact with the dehydrogenation catalyst is performed by continuously passing the gas through a reactor packed with the film-type dehydrogenation catalyst.

EXAMPLES

In the following Examples and Comparative Examples, "%" refers to "% by mass" unless otherwise indicated.

[Alcohol Conversion and Aldehyde Selectivity]

The alcohol conversion and the aldehyde selectivity were calculated in accordance with the following formulae. Table 1 shows the alcohol conversion and the aldehyde selectivity of each of products at 10 hours. For both of the properties, the larger value is better.

Alcohol conversion [%]=100−[GC area % of alcohol]

Aldehyde selectivity [%]=[GC area % of aldehyde]/(100−[GC area % of alcohol])×100.

[Aldehyde Production Rate]

The aldehyde production rate was calculated in accordance with the following formula. In the formula, the alcohol conversion and the aldehyde selectivity are values at 10 hours from the start of alcohol supply. For the aldehyde production rate, the faster is better because the production amount of aldehydes per unit time increases with the production rate.

Aldehyde production rate [g/hour]=[alcohol supply rate [g/hour]]×[alcohol conversion [%]]/100×[aldehyde selectivity [%]]/100

[Dropping Rate of Conversion and Period of Maintaining Conversion]

First, an alcohol conversion of the product at 10 hours from the start of alcohol supply and an alcohol conversion of the product at 20 hours were calculated by the above method, and the dropping rate of conversion was obtained in accordance with the following formula.

Dropping rate of conversion [%/hour]=([alcohol conversion [%] of product at 10 hours]−[alcohol conversion [%] of product at 20 hours])/10 [hours]

Next, the period of maintaining conversion per catalyst unit mass was calculated in accordance with the following formula. For the period of maintaining conversion per catalyst unit mass, the larger value is better because a high conversion can be kept for a long period of time.

Period of maintaining conversion [hour/g]=[alcohol conversion [%] of product at 10 hours]/[dropping rate of conversion [%/hour]]/[packed catalyst amount [g]]

Aldehyde Production Method

Production Example 1

Production of Film-Type Dehydrogenation Catalyst Containing Phenol Resin as Binder Production Step of Powdered Catalyst In a reactor with a reflux cooler, water (300 g), $CuSO_4 \cdot 5H_2O$ (48 g), $FeSO_4 \cdot 7H_2O$ (59 g) and aluminum hydroxide (HIGILITE H-32 manufactured by SHOWA DENKO K.K., 12.14 g) were charged, and heated to 95° C. while stirring. This state was retained for 1 hour while keeping the temperature of the mixture at 95° C. to 97° C. (Cu/Fe (atomic ratio)=1/0.75, Cu/Al of aluminum hydroxide (atomic ratio)=1/0.7). Next, while keeping the temperature, a solution (23% by mass) in which $Na_2CO_3$ (44.8 g, 1 equivalent with respect to the total of equivalent numbers of copper and iron ions) was dissolved in water (150 g) was dropped to the mixture in 80 minutes. A precipitate having a blue-green color, which could be recognized visually in the mixture, gradually discolored to brown, and finally discolored to black.

While keeping the temperature of the mixture at 95° C. to 97° C., a solution 1 (Cu/Fe (atomic ratio)=1/0.75, Cu/Al of aluminum hydroxide (atomic ratio)=1/0.7) in which $CuSO_4 \cdot 5H_2O$ (4.8 g) and $Al_2(SO_4)_3 \cdot 16H_2O$ (46.8 g) were dissolved in water (109.2 g), and a solution 2 (22% by mass, 1 equivalent with respect to the total of equivalent numbers of copper and iron ions) in which $Na_2CO_3$ (27.6 g) was dissolved in water (98.2 g), were dropped to the mixture simultaneously. The dropping of the solution 1 was completed in 60 minutes, and the dropping of the solution 2 was completed in 30 minutes. To this mixture, a solution in which $Al_2(SO_4)_2 \cdot 16H_2O$ (23.4 g) was dissolved in water (53.5 g) was dropped in 30 minutes (Cu/Al of aluminum hydroxide (atomic ratio)=1/2.1). Further, to this mixture, 10% by mass of an NaOH aqueous solution was dropped so as to adjust the mixture at pH 10.5. Then the mixture was aged for 1 hour. After aging, the mixture was filtered under suction to obtain a precipitate. The obtained precipitate was washed three times with 450 mL of water and calcined at 750° C. in air for 1 hour. Thus, a copper-based powdered catalyst was obtained (carrier: HIGILITE H-42M manufactured by SHOWA DENKO K.K., particle diameter of the carrier: 1 µm, copper/iron/aluminum=1/0.75/2.8).

In the following Production Examples, the mass of the binder is a mass of solid content.

(Production Step of Film-Type Dehydrogenation Catalyst)

80 parts by mass of the copper-based powdered catalyst obtained in the above production step of the powdered catalyst, 20 parts by mass of a phenol resin (N210 manufactured by Nihon Gosei Kako Co., Ltd.) as a binder, and 60 parts by mass of methyl ethyl ketone were mixed together in a ball mill to obtain a paint. The paint was coated on one surface of a copper foil (thickness: 40 µm, width: 15 cm×33 cm) (support) using a bar coater. The obtained catalyst layer paint on the copper foil was dried at 130° C. for 1 minute, and then heated at 250° C. in a nitrogen atmosphere for 1 hour to cure the binder in the paint. Similarly to the above, the catalyst layer paint was coated on the other surface of the copper foil, then dried and heated similarly to the above. As a result, a film-type dehydrogenation catalyst in which catalyst layers each having a thickness of 17 µm were fixed on the both surfaces of the copper foil was obtained. The mass of the catalyst layer per unit area including the binder was 21.1 g/m² (the mass of the copper-based catalyst was 16.9 g/m²).

Production Example 2

Production of Pellet-Type Catalyst

The copper-based powdered catalyst obtained in the production step of the powdered catalyst in Production Example 1 above was tablet molded into a columnar shape of (I) 4.8 mm×height 4.7 mm to obtain a pellet-shaped catalyst.

Production Example 3

Production of Film-Type Dehydrogenation Catalyst Containing Phenol Resin as Binder A film-type dehydrogenation catalyst of Production Example 3 was produced in the same manner as in the production step of the film-type dehydrogenation catalyst of Production Example 1, except that a copper/zinc catalyst (X213 manufactured by JGC C&C, copper/zinc=1/0.9) was used instead of the copper-based powdered catalyst obtained in the production step of the powdered catalyst in Production Example 1 above. The mass of the catalyst layer per unit area including the binder was 21.1 g/m² (the mass of the copper-based catalyst was 16.9 g/m²).

Production Example 4

Production of Film-Type Dehydrogenation Catalyst Containing Polyorganosiloxane as Binder 75 parts by mass of the copper-based powdered catalyst obtained in the production step of the powdered catalyst of Production Example 1, 25 parts by mass of a silicon resin (polyorganosiloxane) (trade name "SH805" manufactured by Dow Corning Toray Co., Ltd.) as a binder, and 60 parts by mass of methyl ethyl ketone were mixed together in a ball mill to obtain a paint. The paint was coated on one surface of a copper foil (thickness: 40 µm, width: 15 cm×25 cm) (support) using a bar coater. The obtained catalyst layer paint on the copper foil was dried at 130° C. for 1 minute, and then heated at 250° C. in a nitrogen atmosphere for 90 minutes to cure the binder in the paint. Similarly to the above, the catalyst layer paint was coated on the other surface of the copper foil, then dried and heated similarly to the above. As a result, a film-type dehydrogenation catalyst in which catalyst layers each having a thickness of 20 µm were fixed on the both surfaces of the copper foil was obtained. The mass of the catalyst layer per unit area including the binder was 20.3 g/m², and the mass of the copper-based catalyst of the catalyst layer per unit area was 15.2 g/m². The silicon resin formed a cross-linked structure in the obtained film-type dehydrogenation catalyst.

Production Example 5

Production of Film-Type Dehydrogenation Catalyst Containing Polytitanocarbosilane as Binder A film-type dehydrogenation catalyst of Production Example 5 was produced in the same manner as in the production step of the film-type dehydrogenation catalyst of Production Example 4, except that polytitanocarbosilane (trade name "VN-100" manufactured by UBE INDUSTRIES, LTD.) was used instead of the silicon resin of Production Example 4 above, and the binder was cured in an air atmosphere instead of a nitrogen atmosphere. The mass of the catalyst layer per unit area including the binder was 27.6 g/m², and the mass of the copper-based catalyst of the catalyst layer per unit area was 20.7 g/m². Polytitanocarbosilane formed a cross-linked structure in the obtained film-type dehydrogenation catalyst.

Production Example 6

Production of Film-Type Dehydrogenation Catalyst Containing Polyamide-Imide as Binder A film-type dehydrogenation catalyst of Production Example 6 was produced in the same manner as in the production step of the film-type dehydrogenation catalyst of Production Example 4, except that 90 parts by mass of the copper-based powdered catalyst and 10 parts by mass of polyamide-imide (trade name "HR11NN" manufactured by TOYOBO CO., LTD.) were used instead of 75 parts by mass of the copper-based powdered catalyst and 25 parts by mass of the silicon resin (trade name "SH805" manufactured by Dow Corning Toray Co., Ltd.) of Production Example 4 above, and the obtained catalyst layer paint was not heated after being dried at 130° C. for 1 minute. The mass of the catalyst layer per unit area including the binder was 18.6 g/m², and the mass of the copper-based catalyst of the catalyst layer per unit area was 16.7 g/m². Polyamide-imide formed a cross-linked structure in the obtained film-type dehydrogenation catalyst.

Production Example 7

Production of Film-Type Dehydrogenation Catalyst Containing Polytitanocarbosilane as Binder A film-type dehydrogenation catalyst of Production Example 7 was produced in the same manner as in the production step of the film-type dehydrogenation catalyst of Production Example 5, except that a copper/zinc catalyst (trade name "X213" manufactured by JGC C&C, copper/zinc (atomic ratio)=1/0.9) was used instead of the copper-based powdered catalyst of Production Example 5 above. The mass of the catalyst layer per unit area including the binder was 27.6 g/m², and the mass of the copper-based catalyst of the catalyst layer per unit area was 20.7 g/m². Polytitanocarbosilane formed a cross-linked structure in the obtained film-type dehydrogenation catalyst.

Example 1

Production of n-Octyl Aldehyde Under Partial Pressure of Alcohol of 10 kPa Using the Film-Type Dehydrogenation Catalyst Containing Phenol Resin as Binder The film-type dehydrogenation catalyst obtained in Production Example 1 was bent into a corrugated plate shape. The bent film-type dehydrogenation catalyst and a planar film-type dehydrogenation catalyst were stacked alternately, and packed in a stainless reaction tube 14 (inner diameter: 28 mm, tube length: 150 mm, flow reactor) (packed amount of the powdered catalyst: 3.2 g). A vaporization tube 13 (made of stainless, inner diameter: 2 mm, tube length: 1500 mm) and a gas preheating portion 23 were connected to an inlet of the reaction tube 14, and a cooling tube 16 and a fractionator 17 were connected to an outlet of the reaction tube 14 (see FIG. 1). The vaporization tube 13 and the gas preheating portion 23 were heated at 320° C. for 12 minutes using a heating portion 15. Octyl alcohol (trade name "KALCOL 0898" manufactured by Kao Corporation) was supplied from a starting material alcohol supply portion 11 to the reaction tube 14 via a starting material alcohol supply tube 31 at a speed of 20 g/hour and nitrogen was supplied from a gas supply portion 21 to the reaction tube 14 via a gas supply tube 32 at a speed of 31.8 L/hour. In this case, in the mixed gas of the vaporized octyl alcohol and nitrogen gas, the partial pressure of octyl alcohol was 10 kPa.

Thereafter, the internal temperature of the reaction tube 14 was raised to 240° C. by the heating portion 15. At this time, the reaction pressure was 101 kPa. A product generated inside the reaction tube 14 reached the cooler 16 cooled at 20° C. via a product collection tube 33. The product passed through the cooler 16 was separated in the fractionator 17, and extracted with time via a liquid product collection tube 34. Thus, n-octyl aldehyde was obtained. Table 1 shows evaluation results of the obtained product.

Comparative Example 1

Production of n-Octyl Aldehyde Under Partial Pressure of Alcohol of 10 kPa Using the Pellet-Type Catalyst n-Octyl aldehyde of Comparative Example 1 was obtained by conducting the reaction in the same manner as in Example 1, except that the pellet-type catalyst (catalyst packed amount: 20 g) obtained in Production Example 2 was used instead of the film-type dehydrogenation catalyst obtained in Production Example 1, the reaction temperature was set at 230° C. instead of 240° C., the supply speed of octyl alcohol was set at 24 g/hour instead of 20 g/hour, and the supply speed of nitrogen was set at 40.4 L/hour instead of 31.8 L/hour. Table 1 shows evaluation results of the obtained product.

Comparative Example 2

Production of n-Octyl Aldehyde Under Partial Pressure of Alcohol of 101 kPa Using the Film-Type Dehydrogenation Catalyst Containing Phenol Resin as Binder n-Octyl aldehyde of Comparative Example 2 was obtained by conducting the reaction in the same manner as in Example 1, except that the supply speed of nitrogen was set at 0 L/hour instead of 31.8 L/hour. In this case, in the mixed gas of the vaporized octyl alcohol and nitrogen gas, the partial pressure of octyl alcohol was 101 kPa. Table 1 shows evaluation results of the obtained product.

Example 2

Production of Undecyl Aldehyde Under Partial Pressure of Alcohol of 7 kPa Using the Film-Type Dehydrogenation Catalyst Containing Phenol Resin as Binder The film-type dehydrogenation catalyst obtained in Production Example 1 was bent into a corrugated plate shape. The bent film-type dehydrogenation catalyst and a planar film-type dehydrogenation catalyst were stacked alternately, and packed in the stainless reaction tube 14 (inner diameter: 28 mm, tube length: 150 mm, flow reactor) (packed amount of the powdered catalyst: 3.2 g). The vaporization tube 13 (made of stainless, inner diameter: 2 mm, tube length: 1500 mm) and the gas preheating portion 23 were connected to the inlet of the reaction tube 14, and the cooling tube 16 and the fractionator 17 were connected to the outlet of the reaction tube 14 (see FIG. 1). The vaporization tube 13 and the gas preheating portion 23 were heated at 320° C. for 12 minutes using the heating portion 15. Undecyl alcohol was supplied from the starting material alcohol supply portion 11 to the reaction tube 14 via the starting material alcohol supply tube 31 at a speed of 15 g/hour and nitrogen was supplied from the gas supply portion 21 to the reaction tube 14 via the gas supply tube 32 at a speed of 12.0 L/hour. In this case, in the mixed gas of the vaporized undecyl alcohol and nitrogen gas, the partial pressure of undecyl alcohol was 7 kPa.

Thereafter, the internal temperature of the reaction tube 14 was raised to 220° C. by the heating portion 15. At this time, the reaction pressure was 50 kPa. A product generated inside the reaction tube 14 reached the cooler 16 cooled at 40° C. via the product collection tube 33. The product passed through the cooler 16 was separated in the fractionator 17, and extracted with time via the liquid product collection tube 34. Thus, undecyl aldehyde was obtained. Table 1 shows evaluation results of the obtained product.

Example 3

Production of n-Octyl Aldehyde Under Partial Pressure of Alcohol of 7 kPa Using the Film-Type Dehydrogenation Catalyst Containing Phenol Resin as Binder n-Octyl aldehyde of Example 3 was obtained by conducting the reaction in the same manner as in Example 1, except that the film-type dehydrogenation catalyst (packed amount of the powdered catalyst: 3.5 g) obtained in Production Example 3 was used instead of the film-type dehydrogenation catalyst obtained in Production Example 1, the supply speed of octyl alcohol was set at 12 g/hour instead of 20 g/hour, and the supply speed of nitrogen was set at 27.7 L/hour instead of 31.8 L/hour. In this case, in the mixed gas of the vaporized octyl alcohol and nitrogen gas, the partial pressure of octyl alcohol was 7 kPa. Table 1 shows evaluation results of the obtained product.

Example 4

Production of n-Octyl Aldehyde Under Partial Pressure of Alcohol of 40 kPa Using the Film-Type Dehydrogenation Catalyst Containing Phenol Resin as Binder n-Octyl aldehyde of Example 4 was obtained by conducting the reaction in the same manner as in Example 1, except that the supply speed of nitrogen was set at 4.7 L/hour instead of 31.8 L/hour. In this case, in the mixed gas of the vaporized octyl alcohol and nitrogen gas, the partial pressure of octyl alcohol was 40 kPa. Table 1 shows evaluation results of the obtained product.

Comparative Example 3

Production of n-Octyl Aldehyde Under Partial Pressure of Alcohol of 60 kPa Using the Film-Type Dehydrogenation Catalyst n-Octyl aldehyde of Comparative Example 3 was obtained by conducting the reaction in the same manner as in Example 1, except that the supply speed of nitrogen was set at 2.0 L/hour instead of 31.8 L/hour. In this case, in the mixed gas of the vaporized octyl alcohol and nitrogen gas, the partial pressure of octyl alcohol was 60 kPa. Table 1 shows evaluation results of the obtained product.

Table 1 below summarizes the reaction conditions and results in Examples 1-4 and Comparative Examples 1-3.

It was confirmed from Table 1 that the production methods of Examples could provide target aldehydes with a high conversion for a long period of time as compared with the production methods of Comparative Examples. It also was confirmed that the aldehydes obtained by the production methods of Examples exhibited excellent aldehyde selectivity.

Example 5

Production of n-Octyl Aldehyde Using the Film-Type Dehydrogenation Catalyst Containing Polyorganosiloxane as Binder The film-type dehydrogenation catalyst obtained in Production Example 4 was bent into a corrugated plate shape. The bent film-type dehydrogenation catalyst and a planar film-type dehydrogenation catalyst were stacked alternately, and packed in the stainless reaction tube 14 (inner diameter: 28 mm, tube length: 150 mm, flow reactor) (packed amount of the powdered catalyst: 2.9 g). The vaporization tube 13 (made of stainless, inner diameter: 2 mm, tube length: 1500 mm) and the gas preheating portion 23 were connected to the inlet of the reaction tube 14, and the cooling tube 16 and the fractionator 17 were connected to the outlet of the reaction tube 14 (see FIG. 1). The vaporization tube 13 and the gas preheating portion 23 were heated at 320° C. for 12 minutes using the heating portion 15. Octyl alcohol (trade name "KALCOL 0898" manufactured by Kao Corporation) was supplied from the starting material alcohol supply portion 11 to the reaction tube 14 via the starting material alcohol supply tube 31 at a speed of 20 g/hour and nitrogen was supplied from the gas supply portion 21 to the reaction tube 14 via the gas supply tube 32 at a speed of 31.8 L/hour. In this case, in the gas containing the vaporized octyl alcohol and nitrogen gas, the partial pressure of octyl alcohol was 10 kPa.

Thereafter, the internal temperature of the reaction tube 14 was raised to 240° C. by the heating portion 15. At this time, the reaction pressure was 101 kPa. A product generated inside the reaction tube 14 reached the cooler 16 cooled at 20° C. via the product collection tube 33. The product passed through

TABLE 1

| | | | Example 1 | Comparative Example 1 | Comparative Example 2 | Comparative Example 3 | Example 2 | Example 3 | Example 4 |
|---|---|---|---|---|---|---|---|---|---|
| Reaction conditions | Starting material | | Octyl alcohol | Octyl alcohol | Octyl alcohol | Octyl alcohol | Undecyl alcohol | Octyl alcohol | Octyl alcohol |
| | Catalyst | Form | Film | Pellet | Film | Film | Film | Film | Film |
| | | Metal | CuFeAl | CuFeAl | CuFeAl | CuFeAl | CuFeAl | CuZn | CuFeAl |
| | | Binder | Phenol resin | — | Phenol resin | Phenol resin | Phenol resin | Phenol resin | Phenol resin |
| | Packed catalyst amount | [g] | 3.2 | 20 | 3.2 | 3.2 | 3.2 | 3.5 | 3.2 |
| | Reaction phase | | Gas phase | Gas phase | Gas phase | Gas phase | Gas phase | Gas phase | Gas phase |
| | Partial pressure of alcohol | [kPa] | 10 | 10 | 101 | 60 | 7 | 7 | 40 |
| | Alcohol supply rate | [g/hour] | 20 | 24 | 20 | 20 | 15 | 12 | 20 |
| | Reaction temperature | [° C.] | 240 | 230 | 240 | 240 | 220 | 240 | 240 |
| | Reaction pressure | [kPa] | 101 | 101 | 101 | 101 | 50 | 101 | 101 |
| Results | Alcohol conversion | [%] | 52 | 46 | 30 | 37 | 59 | 49 | 43 |
| | Aldehyde selectivity | [%] | 98 | 90 | 84 | 86 | 95 | 96 | 92 |
| | Aldehyde production rate | [g/hour] | 10.2 | 9.9 | 5.0 | 6.4 | 8.4 | 5.6 | 7.9 |
| | Dropping rate of conversion | [%/hour] | 0.8 | 0.6 | 2.3 | 1.6 | 0.5 | 1.0 | 1.1 |
| | Period of maintaining conversion | [hour/g] | 20.3 | 3.9 | 4.1 | 7.2 | 41.0 | 14.7 | 12.2 | the cooler 16 was separated in the fractionator 17, and extracted with time via the liquid product collection tube 34. Thus, n-octyl aldehyde was obtained. Table 2 shows evaluation results of the obtained product.

Example 6

Production of n-Octyl Aldehyde Using the Film-Type Dehydrogenation Catalyst Containing Polytitanocarbosilane as Binder n-Octyl aldehyde of Example 6 was obtained by conducting the reaction in the same manner as in Example 5, except that the film-type dehydrogenation catalyst (packed amount of the powdered catalyst: 4.0 g) obtained in Production Example 5 was used instead of the film-type dehydrogenation catalyst obtained in Production Example 4. In this case, in the gas containing the vaporized octyl alcohol and nitrogen gas, the partial pressure of octyl alcohol was 10 kPa. Table 2 shows evaluation results of the obtained product.

Example 7

Production of n-Octyl Aldehyde Using the Film-Type Dehydrogenation Catalyst Containing Polyamide-Imide as Binder n-Octyl aldehyde of Example 7 was obtained by conducting the reaction in the same manner as in Example 5, except that the film-type dehydrogenation catalyst (packed amount of the powdered catalyst: 3.2 g) obtained in Production Example 6 was used instead of the film-type dehydrogenation catalyst obtained in Production Example 4. In this case, in the gas containing the vaporized octyl alcohol and nitrogen gas, the partial pressure of octyl alcohol was 10 kPa. Table 2 shows evaluation results of the obtained product.

Example 8

Production of n-Octyl Aldehyde Using the Film-Type Dehydrogenation Catalyst Containing Polytitanocarbosilane as Binder n-Octyl aldehyde of Example 8 was obtained by conducting the reaction in the same manner as in Example 5, except that the film-type dehydrogenation catalyst (packed amount of the powdered catalyst: 2.7 g) obtained in Production Example 7 was used instead of the film-type dehydrogenation catalyst obtained in Production Example 4, the supply speed of octyl alcohol was set at 12 g/hour instead of 20 g/hour, and the supply speed of nitrogen was set at 27.7 L/hour instead of 31.8 L/hour. In this case, in the gas containing the vaporized octyl alcohol and nitrogen gas, the partial pressure of octyl alcohol was 7 kPa. Table 2 shows evaluation results of the obtained product.

Example 9

Production of n-Undecyl Aldehyde Using the Film-Type Dehydrogenation Catalyst Containing Polytitanocarbosilane as Binder The film-type dehydrogenation catalyst obtained in Production Example 5 was bent into a corrugated plate shape. The bent film-type dehydrogenation catalyst and a planar film-type dehydrogenation catalyst were stacked alternately, and packed in the stainless reaction tube 14 (inner diameter: 28 mm, tube length: 150 mm, flow reactor) (packed amount of the powdered catalyst: 4.0 g). The vaporization tube 13 (made of stainless, inner diameter: 2 mm, tube length: 1500 mm) and the gas preheating portion 23 were connected to the inlet of the reaction tube 14, and the cooling tube 16 and the fractionator 17 were connected to the outlet of the reaction tube 14 (see FIG. 1). The vaporization tube 13 and the gas preheating portion 23 were heated at 320° C. for 12 minutes using the heating portion 15. Undecyl alcohol was supplied from the starting material alcohol supply portion 11 to the reaction tube 14 via the starting material alcohol supply tube 31 at a speed of 28 g/hour and nitrogen was supplied from the gas supply portion 21 to the reaction tube 14 via the gas supply tube 32 at a speed of 3.6 L/hour. In this case, in the gas containing the vaporized undecyl alcohol and nitrogen gas, the partial pressure of undecyl alcohol was 7 kPa.

Thereafter, the internal temperature of the reaction tube 14 was raised to 240° C. by the heating portion 15. At this time, the reaction pressure was 20 kPa. A product generated inside the reaction tube 14 reached the cooler 16 cooled at 40° C. via the product collection tube 33. The product passed through the cooler 16 was separated in the fractionator 17, and extracted with time via the liquid product collection tube 34. Thus, n-undecyl aldehyde was obtained. Table 2 shows evaluation results of the obtained product.

Table 2 below summarizes the reaction conditions and results in Examples 5-9.

TABLE 2

| | | | Example 5 | Example 6 | Example 7 | Example 8 | Example 9 |
|---|---|---|---|---|---|---|---|
| Reaction conditions | Starting material | | Octyl alcohol | Octyl alcohol | Octyl alcohol | Octyl alcohol | Undecyl alcohol |
| | Film-type dehydrogenation catalyst | | Production Example 4 | Production Example 5 | Production Example 6 | Production Example 7 | Production Example 5 |
| | Catalyst | Metal | CuFeAl | CuFeAl | CuFeAl | CuZn | CuFeAl |
| | | Binder | Poly-organosiloxane | Poly-titanocarbosilane | Polyamide-imide | Poly-titanocarbosilane | Polytitanocarbosilane |
| | Packed catalyst amount | [g] | 2.9 | 4.0 | 3.2 | 2.7 | 4.0 |
| | Partial pressure of alcohol | [kPa] | 10.0 | 10.0 | 10.0 | 7.0 | 7.0 |
| | Alcohol supply rate | [g/hour] | 20 | 20 | 20 | 12 | 28 |
| | Reaction temperature | [° C.] | 240 | 240 | 240 | 240 | 240 |
| | Reaction pressure | [kPa] | 101 | 101 | 101 | 101 | 20 |
| Results | Alcohol conversion | [%] | 68 | 68 | 55 | 65 | 56 |
| | Aldehyde selectivity | [%] | 99 | 98 | 96 | 98 | 97 |
| | Aldehyde production rate | [g/hour] | 13.3 | 13.2 | 10.6 | 7.6 | 15.2 |
| | Dropping rate of conversion | [%/hour] | 0.7 | 0.3 | 5.4 | 0.5 | 0.3 |
| | Period of maintaining conversion | [h/g] | 35.8 | 67.6 | 3.2 | 48.0 | 56.1 |

It was confirmed from Table 2 that the production methods of Examples 5-9 could provide target aldehydes with a high initial conversion (conversion at 10 hours) as compared with the production methods of Comparative Examples and Examples 1, 3. It also was confirmed that the production methods of Examples 5-9 could keep a high conversion for a long period of time.

INDUSTRIAL APPLICABILITY

According to the production method of the present invention, target aldehydes can be obtained with a high conversion for a long period of time, and the aldehyde selectivity of the obtained aldehydes is excellent. Therefore, it is possible to produce aldehydes, especially primary aldehyde, with high efficiency and high purity. Such a production method can be used suitably as a production method of aldehydes useful as fragrance materials.

Moreover, according to the production method of the present invention in which a dehydrogenation catalyst is a film-type dehydrogenation catalyst that is formed by providing on a support a thin film catalyst layer containing a powdered catalyst and a silicon-containing resin as a binder, it is possible to obtain target aldehydes with a high initial conversion and keep a high conversion for a long period of time. Therefore, it is possible to produce aldehydes, especially primary aldehyde, with high efficiency and high purity. Such a production method can be used suitably as a production method of aldehydes useful as fragrance materials.

DESCRIPTION OF REFERENCE NUMERALS 11 starting material alcohol supply portion
12 starting material supply pump
13 vaporization tube
14 reaction tube
15 heating portion
16 cooling tube
17 fractionator
21 gas supply portion
22 gas flow rate regulator
23 gas preheating portion
31 starting material alcohol supply tube
32 gas supply tube
33 product collection tube
34 liquid product collection tube
35 exhaust gas discharge tube

The invention claimed is:

1. A method for producing an aldehyde, comprising bringing a mixed gas containing a vaporized primary alcohol and an inert gas into contact with a film-type dehydrogenation catalyst so as to dehydrogenate the primary alcohol in the mixed gas, thereby obtaining an aldehyde, the partial pressure of the primary alcohol in the mixed gas being 50 kPa or lower, and the film-type dehydrogenation catalyst being formed by providing a thin film catalyst layer on a support.

2. The method for producing an aldehyde according to claim 1, wherein the dehydrogenation catalyst comprises copper as an active species.

3. The method for producing an aldehyde according to claim 2, wherein the dehydrogenation catalyst further comprises zinc or iron as an active species.

4. The method for producing an aldehyde according to claim 1, wherein the inert gas contains nitrogen or a rare gas.

5. The method for producing an aldehyde according to claim 1, wherein the reaction temperature is in a range of 200° C. to 300° C.

6. The method for producing an aldehyde according to claim 1, wherein the reaction pressure is in a range of 10 kPa to 102 kPa.

7. The method for producing an aldehyde according to claim 2, wherein the dehydrogenation catalyst is supported on a carrier.

8. The method for producing an aldehyde according to claim 7, wherein the carrier is an oxide or a hydroxide of zinc or aluminum.

9. The method for producing an aldehyde according to claim 1, wherein the primary alcohol is a saturated aliphatic alcohol with a carbon number of 4 to 18.

10. The method for producing an aldehyde according to claim 1, wherein the dehydrogenation catalyst is a film-type dehydrogenation catalyst that is formed by providing on a support a thin film catalyst layer containing a powdered catalyst and a silicon-containing resin as a binder.

11. The method for producing an aldehyde according to claim 10, wherein the silicon-containing resin is polycarbosilane, polysiloxane, polyborosiloxane, polytitanosiloxane, polysilazane, polyorganoaminosilane, polysilastyrene, polytitanocarbosilane, polyzirconocarbosilane, or polyorganosiloxane.

12. The method for producing an aldehyde according to claim 10, wherein the film-type dehydrogenation catalyst is a catalyst obtained by coating the support with a mixture of the powdered catalyst and the silicon-containing resin and curing the silicon-containing resin to fix the powdered catalyst on the support.

13. The method for producing an aldehyde according to claim 1, wherein the step of bringing the gas into contact with the dehydrogenation catalyst is performed by continuously passing the gas through a reactor packed with the film-type dehydrogenation catalyst.

14. The method for producing an aldehyde according to claim 10, wherein the weight ratio of the powdered catalyst and the silicon-containing resin (the powdered catalyst:the silicon-containing resin) is 85:15 to 15:85.

15. The method for producing an aldehyde according to claim 10, wherein the silicon-containing resin has a cross-linked structure.

16. The method for producing an aldehyde according to claim 1, wherein the primary alcohol is a saturated aliphatic alcohol with a carbon number of 6 to 12.

17. The method for producing an aldehyde according to claim 10, wherein the powdered catalyst is a copper-based powdered catalyst.

18. The method for producing an aldehyde according to claim 10, wherein the powdered catalyst as a composition containing a carrier is a catalyst containing copper-iron-aluminum (CuFeAl).

19. The method for producing an aldehyde according to claim 10, wherein the atomic ratio of copper/iron/aluminum (copper/iron/aluminum) is 1/0.4-2.5/0.5-5.0.

20. The method for producing an aldehyde according to claim 10, wherein the silicon-containing resin is polyorganosiloxane or polytitanocarbosilane.

* * * * *

UNITED STATES PATENT AND TRADEMARK OFFICE
CERTIFICATE OF CORRECTION

PATENT NO.        : 9,315,439 B2  
APPLICATION NO.   : 14/411315  
DATED             : April 19, 2016  
INVENTOR(S)       : Tsubasa Arai et al.

Page 1 of 1

It is certified that error appears in the above-identified patent and that said Letters Patent is hereby corrected as shown below:

On the title page, Item 73, "KaoCorporation, Tokyo (JP)" should read --Kao Corporation, Tokyo (JP)--

Signed and Sealed this  
Sixteenth Day of August, 2016

Michelle K. Lee  
*Director of the United States Patent and Trademark Office*